(12) United States Patent
Balde

(10) Patent No.: US 8,703,213 B2
(45) Date of Patent: Apr. 22, 2014

(54) **ANTI-DIABETIC COMPOSITION CONTAINING A PLANT EXTRACT OF *ENGLERINA LECARDII***

(76) Inventor: Aliou Mamadou Balde, Conakry (GN)

( * ) Notice: Subject to any disclaimer, the term of this patent is extended or adjusted under 35 U.S.C. 154(b) by 59 days.

(21) Appl. No.: 13/511,411

(22) PCT Filed: Nov. 23, 2010

(86) PCT No.: PCT/IB2010/055374
§ 371 (c)(1),
(2), (4) Date: Aug. 13, 2012

(87) PCT Pub. No.: WO2011/061725
PCT Pub. Date: May 26, 2011

(65) Prior Publication Data
US 2012/0315327 A1 Dec. 13, 2012

(30) Foreign Application Priority Data
Nov. 23, 2009 (FR) ..................................... 09 05623

(51) Int. Cl.
*A61K 36/185* (2006.01)
*A61K 9/00* (2006.01)
*A61P 3/10* (2006.01)

(52) U.S. Cl.
USPC ........... 424/725; 424/400; 424/452; 424/456; 424/774

(58) Field of Classification Search
None
See application file for complete search history.

(56) References Cited

U.S. PATENT DOCUMENTS

2005/0181078 A1 * 8/2005 Kawamura .................... 424/725

FOREIGN PATENT DOCUMENTS

| EP | 1278514 B1 * 10/2006 |
| WO | 01/60389 A2 8/2001 |
| WO | WO 2009001362 A2 * 12/2008 |

OTHER PUBLICATIONS

Arbonnier, Micheal, Trees, Shrubs, and Lianas of West African dry zones, Margraf Publishers, published 2004, p. 345-346.*
About Herbal Extracts, https://www.theherbalist.com/about-herbal-extracts.html, information provided by internet archive wayback machine http://archive.org/web/web/php Sep. 28, 2008.*
Hoffman, Medical Herbalism: The science and practice of herbal medicine, healing arts press 2003, p. 223-224.*
Gaby, Alan MD, Integrative Medicine, vol. 5, No. 4 Aug./ Sep. 2006.*
Ojewole (Ojewole, J. A., et al., Hypoglycaemic and hypotensive effects of Globimetula cupulata (DC) Van Tieghem (Loranthaceae) aqueous leaf extract in rats, Cardiovasc. J. S. Africa, 18 (2007) p. 9-15).*
Boussim (Boussim, I.L., et al., Mistletoes of the agroforestry parklands of Burkina Faso, Agroforestry Systems, 60 (2004) p. 39-49).*
Boly (Boly, R., et al., Quercetin inhibits a large panel of kinases implicated in cancer cell biology, Int. J. Oncol., 38 (2011), p. 833-842).*
International Search Report and Written Opinion issued by the International Searching Authority dated Feb. 10, 2011 for International Application No. PCT/IB2010/055374.
Gray, A M et al. "Insulin-secreting activity of the traditional antidiabetic plant *Viscum album* (mistletoe)", *Journal of Endocrinology*; 1999; vol. 160; No. 3; pp. 409-414; Society for Endocrinology; Great Britain.
Obatomi, D.K. et al. "Reduction in serum glucose and cholesterol levels in experimental diabetic rats treated with extracts of African mistletoe (*Loranthus begwensis*)"; *Medical Science Research*; 1997; vol. 25; No. 1; pp. 651-654; Chapman & Hall.
Hummel, Michael et al. "Clinical Studies on Chromium Supplementation in Diabetes Mellitus"; *Current Topics in Nutraceutical Research*; 2009; vol. 7, No. 1, pp. 1-10; New Century Health Publishers, LLC.

* cited by examiner

*Primary Examiner* — Rachael E Bredefeld
*Assistant Examiner* — Dominic Lazaro
(74) *Attorney, Agent, or Firm* — Heslin Rothenberg Farley & Mesiti P.C.

(57) ABSTRACT

The invention relates to a pharmaceutical antidiabetic composition containing, among the active ingredients thereof, a plant extract of *Englerina lecardii*, preferably a hydroalcoholic extract of *Englerina lecardii* leaves. The composition is preferably formulated in the form of microspheres produced using an extrusion and spheronisation method, and then grouped together in capsules. In particular, the composition is intended for cases of type 2 diabetes.

11 Claims, No Drawings

ANTI-DIABETIC COMPOSITION CONTAINING A PLANT EXTRACT OF *ENGLERINA LECARDII*

CROSS REFERENCE TO RELATED APPLICATIONS

This application is a national stage filing under section 371 of International Application No. PCT/IB2010/055374, filed on Nov. 23, 2010, and published on May 26, 2011, as WO/2011/061725, and claims priority to French Application No. 09 05623 filed on Nov. 23, 2009.

The present invention relates to the use of an herbal extract of *Englerina lecardii* for manufacturing a pharmaceutical composition for the treatment of diabetes, more particularly for treatment of type II diabetes.

Diabetes is a chronic disease that appears when the pancreas does not secrete enough insulin, in which case it is known as type I diabetes, or when the organism makes poor use of the insulin that it produces, in which case it is known as type II diabetes. Insulin is a hormone that regulates the concentration of glucose in the blood. Hyperglycemia, corresponding to too-high concentration of glucose in the blood, is a common effect of diabetes, which in time causes severe lesions that may affect numerous parts of the body, especially the heart, the blood vessels, the eyes, the kidneys or the nerves.

Type II diabetes represents 90% of the cases of diabetes throughout the world and results mainly from problems of diet, overweight, lack of physical exercise and genetic factors. Type I diabetes, fortunately less common, rapidly leads to death without daily administration of insulin.

The World Health Organization (WHO) estimates that there are more than 180 million diabetics in the world, including 4 million in France alone, and that this number will more than double by 2030. According to estimates, 1.1 million persons died of diabetes in 2005, and the WHO predicts that deaths due to diabetes will increase by more than 50% in the next ten years unless urgent measures are taken.

Diabetes and its complications also have serious economic and social consequences for the patients, their family, the health systems and the nations concerned.

At present, the most widely used treatment for diabetes consists in administering a glucophage to the patient. This is generally metformin, a chemical substance obtained by semi-synthesis from a plant known as *Galega*.

The metformin molecule, commonly used in the form of tablets, has several disadvantages.

Firstly it has numerous medical contraindications. In particular, metformin is contraindicated in cases of acidoketosic diabetes, of diabetic pre-coma, of even moderate kidney disorders (or of pathologies causing them), of liver disorders, of exploratory procedures using iodine contrast products, of heart failure or of respiratory failure. It must not be administered to children or to nursing women, and may be taken only under medical supervision by elderly subjects and pregnant women. Finally, the prolonged use of metformin potentiates the risk of appearance of its adverse effects.

In addition, metformin may cause numerous adverse effects, especially gastrointestinal symptoms such as nausea, vomiting, diarrhea, abdominal pains and loss of appetite. Other effects observed in some individuals include mild erythema, reduced absorption of vitamin B12 accompanied by low serum levels and lactic acidosis, in the most serious cases with acidosic dyspnea, abdominal pains and hypothermia followed by coma.

Difficult to measure correctly depending on each individual, metformin, in case of overdose, may also cause an excessive drop of blood glucose, with consequences just as serious as hyperglycemia.

In addition, metformin is an expensive drug, which causes a serious economic problem for diabetics from the poorest countries. In fact, it must not be overlooked that more than 80% of the deaths due to diabetes occur in countries with low or moderate income. But the high cost of traditional antidiabetes treatments makes access difficult in developing countries. Access to antidiabetes treatment is therefore limited to a very small part of the affected population.

Finally, metformin is a sensitive molecule, which necessitates strict storage conditions, which is extremely problematic in hot and/or humid countries, especially in Africa and Asia.

In these countries, especially in Africa, it would be particularly beneficial to have an effective and much less expensive treatment, obtained from local plants and in a form that does not cause storage problems.

This is the aim of the invention, the object of which is to provide an effective medication, generating far fewer side effects and the cost of which would remain low compared with the cost of the current antidiabetic drugs.

To solve this technical problem, the invention teaches the use of an herbal extract of *Englerina lecardii* for manufacturing a pharmaceutical composition for the treatment of diabetes.

Advantageously, the composition according to the invention exhibits zero or very few side effects and is much less expensive than the traditional antidiabetes medications. Thus it is accepted much more readily by the patients for regular long-term treatment.

It is particularly effective in cases of type II diabetes, which represents the most common type of diabetes.

It has a function of stimulating the pancreas permitting the patient himself or herself to secrete the sufficient quantity of insulin necessary for his or her health. Studies have shown that the antidiabetic pharmaceutical composition of the invention makes it possible to treat diabetes starting from a glucose level of 1.05 g/L in the blood.

Since the active principle of the antidiabetic pharmaceutical composition of the invention is obtained directly from a natural herbal extract, without chemical modification of its molecules, it is tolerated much better by the organism and causes fewer side effects.

In addition, its effect is potentiated by the other plant components that are present in the herbal extract and that are mixed with the active principle during preparation of the therapeutic composition.

In addition, and as is frequent with natural herbal extracts that have not been chemically modified, the active principle of the antidiabetic pharmaceutical composition of the invention has very low risks of overdose, thus considerably reducing the risk of excessive hypoglycemia related to ingestion of the medication.

Other characteristics and advantages of the invention will become apparent from reading the detailed description hereinafter.

*Englerina lecardii* or *Loranthus lecardii*, the common name of which is sattaga bowal, is a semi-parasitic subligneous plant of the Loranthaceae family. It flourishes on savannah trees and is widely distributed in Senegal, Mali, Guinea-Bissau and in Guinea. It has petiolate opposed or sub-opposed leaves; and an oval to elliptical or lanceolate foliar leaf blade, with cuneate base and glabrous and penninerved, acute to subacuminate apex, exhibiting four to six pairs of lateral ribs. Its flowers are bright golden yellow, with stalk 2.2 to 2.7 cm long, shortly pedicellate, grouped in pedunculate umbels, axillary and with perianth slit on one side. It produces ovoid bacciform fruits of 6 to 9 mm length, which are red when ripe.

The therapeutic composition according to the invention is obtained by using an herbal extract of *Englerina lecardii*. This extract is preferably obtained from *Englerina lecardii* leaves, and has a hypoglycemic activity as well as an antioxidant and cytoprotective phytotherapeutic effect.

The fact that the leaves of the plant are used to obtain the herbal extract is advantageous, because removal of these leaves does not destroy the plant, which is therefore able to continue producing other leaves usable for making the pharmaceutical composition of the invention. Nevertheless, other parts of the *Englerina lecardii* plant could be used additionally or alternatively to obtain the composition according to the invention.

The herbal extract of *Englerina lecardii* leaves contains numerous active principles, several of which have been identified. In order to study the chemical composition of this extract, phytochemical screening was carried out by means of general tests and by thin-layer chromatography. It made it possible to reveal that the herbal extract of *Englerina lecardii* contains proanthocyanidines, saponisides, reducing compounds and carotenoids. Column chromatography made it possible to detect the presence of oligosaccharides and a high proportion of polyphenols.

The herbal extract of *Englerina lecardii* used in the scope of the invention is preferably an herbal solution or a liquid herbal extract and, for example depending on its concentration, a mother tincture, an officinal tincture or a liquid extract of *Englerina lecardii*.

This solution or liquid extract is obtained by any appropriate means and especially by extraction, preferably with water, alcohol or aqueous alcohol, by maceration, infusion, decoction, digestion, leaching or similar method.

According to one preferred embodiment of the invention, a liquid herbal extract is prepared from *Englerina lecardii* leaves by means of extraction with aqueous alcohol, using a technique of percolation with agitation. Its alcohol content is preferably between 30 and 70%.

As an example, a mother tincture of *Englerina lecardii* with an ethanol content of approximately 70% V/V was prepared from dry *Englerina lecardii* leaves by exhaustive percolation in the cold followed by concentration under vacuum in a rotary evaporator.

The composition according to the invention may have different galenical forms. For example, it may have the form of tea bags containing, for example, approximately 5 grams of coarsely crushed *Englerina lecardii* leaves.

It may also have the form of tablets, preferably orodispersible, of soft capsules, granules, gelcaps, powder, ampoules, syrup or any other appropriate galenical form, preferably oral, that can be imagined by the person skilled in the art.

Preferably the composition according to the invention is formulated in the form of microspheres, also known as spheroids, preferably filled into gelcaps in a quantity corresponding, for example, to a unit dose.

This provides the benefit of the numerous advantages of this galenical form, namely on the medical level a rapid release and a great bioavailability of the active principles, and on the practical level a great ease of use for the patient and a fairly insensitive form that is very stable for prolonged periods even under difficult storage conditions.

These microspheres may be produced by different methods.

A first method consists, for example, in forming a peripheral layer containing the herbal extract of *Englerina lecardii* around a neutral core, formed, for example, from a mixture of sugar and starch or from a crystal of sugar, mannitol or sorbitol.

The layer containing the herbal extract of *Englerina lecardii* may advantageously be formed by coating, impregnation, pulverization or spraying, the active principle preferably being mixed with a fixing agent or binder for that purpose.

According to a second preferred method, the microspheres or spheroids may be formed by extrusion and spheronization.

For that purpose the herbal extract of *Englerina lecardii* is first mixed with an absorbent or adsorbent substance, preferably of natural or synthetic polymeric type, having plastic properties compatible with the steps of extrusion and spheronization of the sequence of the method.

For example, this is the case of microcrystalline cellulose, of microfine cellulose, of a slightly substituted hydroxypropyl cellulose polymer, of starch, of modified starch, of polysaccharides or of any other appropriate substance or mixture.

If the mixture is too dry, an aqueous or non-aqueous moistening liquid may also be added to obtain a homogeneous malleable paste that can be subjected to the ensuing steps of the method.

The moistening liquid also functions as a vehicle for transporting and depositing the active principle as far as the core of the absorbent and adsorbent substance, into the microcavities of the polymer.

The manufacturing method then consists in extruding the moist mass through a die with appropriately sized orifices. In this way there are obtained compact filaments of generally cylindrical and precise cross section, known as "extrudates".

These "extrudates" are then placed in a cylindrical apparatus known as a "spheronizer", containing in its lower part a grooved disk turning at variable and controlled speed. Under the effect of the centrifugal force exerted by the rotation of the turning disk, the "extrudates" are regularly fragmented then transformed to spheres by a rolling-bonding effect. In this way the desired spheroids are obtained.

These two methods may additionally comprise at least one drying step and/or one sizing step.

Drying may be accomplished by gentle heating, for example at a temperature between 30 and 40° C. or by simple exposure to the open air for a sufficient duration.

Finally, the resulting spheroids may be optionally coated on the periphery by an external film with a view to protecting them, for example, from external moisture, heat, aggressive conditions of the organism or conditions having a delaying effect.

The present inventors discovered that the herbal extract of *Englerina lecardii* leaves advantageously has antibacterial, cytoprotective and antioxidant properties in addition to its antidiabetic properties.

Biological studies have made it possible to show that the nonpolar extract of *Englerina lecardii* leaves in chloroform and/or ethyl acetate is active against *Trypanosoma cruzi* with an MIC (minimum inhibitory concentration) of 2.05 to 2.9 µg/mL and against *T. brucei* with an MIC of 2.18 µg/mL. Antiplasmodial activity against *Plasmodium falciparum* (MIC=16.91 µg/mL) and modest activity against *Staphylococcus aureus* (MIC=29.11 µg/mL) also are noted.

The polar extract of *Englerina lecardii* leaves in methanol exhibits modest activity on *Candida albicans*, with an MIC equal to 28.12 µg/mL.

As regards the antidiabetic properties of the composition according to the invention, the present inventors have carried out two studies that have made it possible to conclude that the blood glucose of diabetic patients treated with a decoction of *Englerina lecardii* leaves is substantially lowered.

The first study is a preliminary ethnotherapeutic evaluation, which was conducted on sixteen diabetic patients (nine men and seven women) with ages from 36 to 70 years.

For a period of eight weeks, these patients received three doses per day of *Englerina lecardii* herbal extract in the form of tea bags containing 5 g of coarsely crushed *Englerina lecardii* leaves, This treatment made it possible to achieve substantial lowering of the blood glucose level in thirteen patients. The progressive reductions of the mean blood glucose levels were as follows: 2.18 g/L; 1.86 g/L, 1.57 g/L, 1.25 g/L and 1.11 g/L.

The second study is a clinical trial conducted in the Department of Endocrinology, Diabetology and Metabolic Diseases of DONKA National Hospital at Conakry in Guinea. This controlled clinical trial demonstrated the efficacy and good tolerance of a composition based on *Englerina lecardii* in the treatment of diabetes in adults. The details of this trial are presented below.

The patients included in the trial were treated with three tea bags containing 5 g of *Englerina lecardii* leaves per day over a period of three months.

Of 31 subjects included initially, 25 subjects (nine men and sixteen women; mean age: 49 years) participated in the trial until its end. Four patients dropped out after inclusion and two patients stopped participating in the trials for personal reasons. In three cases, intermediate laboratory data (transaminases, bilirubin, venous blood glucose) were not received for tangible reasons (samples not analyzed because of lack of electricity).

Efficacy

The mean blood glucose levels before inclusion and after six and twelve weeks of treatment are presented in Table I below.

It is evident from this table that the fasting blood glucose level was lowered on average by 80 mg/dL (205 mg/dL on average at inclusion compared with 125 mg/dL on average after twelve weeks of treatment; $p<0.001$).

TABLE I

Evolution of the means after 6 and 12 weeks of treatment with *Englerina lecardii* and comparison after 12 weeks of treatment with *Englerina lecardii* of parameters for evaluating the efficacy (n = 25 subjects)

| Variables | Inclusion | 6 weeks | 12 weeks | Absolute difference (%)* | p** |
|---|---|---|---|---|---|
| Weight (kg) | 77.28 | 77.32 | 76.81 | −0.47 (−0.61%) | 0.41 |
| Body mass index (kg/m$^2$) | 28.94 | 28.98 | 28.70 | −0.24 (−0.83%) | 0.53 |
| Systolic arterial pressure (mm Hg) | 128.8 | 125.6 | 123.2 | −5.6 (−4.35%) | 0.07 |
| Diastolic arterial pressure (mm Hg) | 83.2 | 82.8 | 80.8 | −2.4 (−2.88%) | 0.27 |
| Fasting blood glucose (g/L) | 2.05 | 1.51 | 1.25 | −0.80 (−39.02%) | <0.001 |

*Between the values at inclusion and those observed after twelve weeks of treatment
**Comparison by t test.

Tolerance

In addition to the efficacy of the treatment, its tolerance was also evaluated both clinically and biologically during this trial.

Clinically, ten patients (corresponding to 40% of the subjects tested) reported side effects: diarrhea in four cases (16%), a bitter taste during ingestion in two cases (8%), accentuation of polyuria in one case (4%), dryness of the mouth in one case (4%), diurnal drowsiness and a feeling of "lightheadedness" without concomitant hypoglycemia in one case (4%).

Biologically, parameters for monitoring the biological tolerance were measured at inclusion, then after six and twelve weeks of treatment. The evolution of these parameters is presented in Table II below.

TABLE II

Evolution of the means after 6 and 12 weeks of treatment with *Englerina lecardii* and comparison after 12 weeks of treatment with *Englerina lecardii* of parameters for evaluating the tolerance (n = 25 subjects)

| Variables | Inclusion | 6 weeks | 12 weeks | Absolute difference (%)* | p** |
|---|---|---|---|---|---|
| ALAT level (IU/L) | 7.15 | 6.42 | 6.47 | −0.68 (−9.51%) | 0.73 |
| ASAT level (IU/L) | 7.43 | 12.47 | 7.57 | 0.14 (+1.88%) | 0.89 |
| Bilirubin (mmol/L) | 13.26 | 11.77 | 11.16 | −2.10 (−15.84%) | 0.31 |
| Blood creatinine (mmol/L) | 72.11 | 67.08 | 88.80 | +16.69 (+23.15%) | 0.38 |

*Between the values at inclusion and those observed after twelve weeks of treatment.
**Comparison by t test.

No anomaly in blood count was observed during the trial. Slight elevation of the creatinine level (72.11 mmol/L at inclusion compared with 88.8 mmol/L after 12 weeks of treatment) was observed, without associated proteinuria. The following parameters: weight, waist circumference, hip circumference and systolic and diastolic arterial pressures, transaminases (AST and ALT) and bilirubin, did not vary significantly.

In total, no major adverse effect was reported. The majority of the clinical side effects reported are of digestive nature (diarrhea) or are probably related to the method of administration (bitter taste during ingestion). The symptoms of polyuria (6%) and dryness of the mouth (6%) may be related to the hyperglycemia itself. The diurnal drowsiness and the feeling of "lightheadedness" reported by one subject remained unexplained, all the more so because it was not possible to attribute them to hypoglycemia.

Biologically, the blood creatinine levels were higher than the base levels (21% for the subjects at the end of the trial; 18% for the subjects at the midpoint of the treatment). However, no subject reached a creatinine level capable of causing renal toxicity. The transaminase levels remained within the limits of the normal value, while the mean bilirubin level rose at the end of 6 weeks of treatment before declining after 12 weeks of treatment.

Consequently, a decline of approximately 0.8 g/L of the blood glucose level can be observed by virtue of the administration of *Englerina lecardii*, which seems to be clinically interesting. The hypoglycemic effect suggested during the preliminary ethnotherapeutic study is therefore confirmed. The decline in blood glucose is progressive and is observed without weight gain.

In addition to the herbal extract of *Englerina lecardii*, the composition according to the invention may contain one or more other appropriate compounds or excipients such as, for example, extracts of one or more other plants, vitamins, minerals, oligoelements, compounds that enhance the efficacy of the active principle, that protect or aid it during its rapid release, flavorings, fixing agents, binder compounds, glidant compounds, lubricant compounds, surfactants, sugars, lactose, sorbitol, mannitol, starches or modified starches, maltodextrins, carbonates, citrates, gelatin, polyvinylpyrrolidone, polysaccharides, cellulose derivatives, cross-linked sodium carboxymethyl cellulose, microcrystalline cellulose, microfine cellulose, slightly substituted hydroxypropyl cellulose polymers or any other appropriate compound.

The following example will permit better illustration of the invention.

Spheroids were prepared by the method of extrusion and spheronization described in the foregoing, starting with an aqueous alcoholic extract of Englerina lecardii leaves prepared according to the European Pharmacopoeia, with an ethanol content of 70% V/V and a dry residue of approximately 10%. These spheroids were filled into 350 mg gelcaps.

EXAMPLE

For One 350 mg Gelcap:
  *Englerina lecardii* extract 350 mL dry residue equivalent 35 mg
  microcellulose q.s.

The spheroids obtained were filled into 350 mg gelcaps, corresponding to a unit dose of the composition, for a preferred dosage of three gelcaps per day.

It is clarified here that chromium may be added to the formula in variable proportions acceptable to and tolerable by the human organism in accordance with the directives of the WHO, World Health Organization.

This oligoelement is a facilitator that makes it possible to activate the fight against diabetes.

This incorporation may be achieved in different ways, including simple addition to the extract or to the microcrystalline cellulose powder or else to the moistening liquid.

Obviously the invention is not limited to the preferred embodiments described in the foregoing, the person skilled in the art being able to make numerous modifications thereto and to conceive of other variants without departing from the scope or the context of the invention defined by the claims.

The invention claimed is:

1. A method for treating type II diabetes, said method comprising administering to a patient in need thereof an herbal extract of *Englerina lecardii*, wherein the patient in need thereof is a patient diagnosed with type II diabetes.

2. The method according to claim 1, wherein the herbal extract of *Englerina lecardii* is obtained from *Englerina lecardii* leaves.

3. The method according to claim 2, wherein the herbal extract of *Englerina lecardii* is an aqueous alcoholic extract of *Englerina lecardii* leaves.

4. The method according to claim 3, wherein the herbal extract of *Englerina lecardii* is a mother tincture of *Englerina lecardii* with an ethanol content of approximately 70% V/V.

5. The method according to claim 1, wherein the herbal extract is administered together with one or more compounds or ingredients selected from herbal extracts, vitamins, minerals, oligoelements, compounds that enhance the efficacy of the active principal, that protect or aid it during its rapid release, flavorings, fixing agents, binder compounds, glidant compounds, lubricant compounds, surfactants, sugars, lactose, sorbitol, mannitol, starches and modified starches, maltodextrins, carbonates, citrates, gelatin, polyvinylpyrrolidone, polysaccharides, cellulose derivatives, cross-linked sodium carboxymethyl cellulose, microcrystalline cellulose, micro-fine cellulose, and substituted hydroxypropyl cellulose polymers.

6. The method according to claim 1, wherein the herbal extract is administered in an oral galenical form.

7. The method according to claim 1, wherein the herbal extract is administered together with chromium.

8. The method according to claim 6, wherein the galenical form is selected from a tea bag, microsphere, tablet, orodispersible tablet, soft capsule, granule, gelcap, powder, ampoule and syrup.

9. The method according to claim 8, wherein the galenical form is a tea bag containing approximately five grams of coarsely crushed *Englerina lecardii* leaves.

10. The method according to claim 8, wherein the galenical form is micro-spheres obtained by a method of extrusion and spheronization.

11. The method according to claim 10, wherein the microspheres are contained within a gelcap.

* * * * *